United States Patent [19]
Plotkin et al.

[11] Patent Number: 5,227,533
[45] Date of Patent: Jul. 13, 1993

[54] ALK-1-ENYL ETHERS

[75] Inventors: Jeffrey S. Plotkin, Monsey, N.Y.; Kolazi S. Narayanan, Palisades Park; Paul D. Taylor, West Milford, both of N.J.

[73] Assignee: ISP Investments Inc., Wilmington, Del.

[21] Appl. No.: 867,562

[22] Filed: Apr. 13, 1992

Related U.S. Application Data

[63] Continuation-in-part of Ser. No. 417,135, Oct. 4, 1989, abandoned.

[51] Int. Cl.$^5$ ............................................. C07C 41/00
[52] U.S. Cl. ..................................... 568/637; 568/636; 568/673; 568/674
[58] Field of Search ............... 568/616, 636, 637, 673, 568/674

[56] References Cited

U.S. PATENT DOCUMENTS
4,703,114  10/1987  Mori .................................... 568/616

FOREIGN PATENT DOCUMENTS
54/14525  2/1979  Japan .

OTHER PUBLICATIONS
Gigg, R. J. Chem. Soc. London Perkins I(3) 712–718, 1979.

Primary Examiner—Paul J. Killos
Attorney, Agent, or Firm—Marilyn J. Maue; Joshua J. Ward

[57] ABSTRACT

This invention relates to the alk-1-enyl ether having the formula

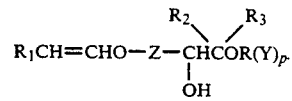

13 Claims, No Drawings

ALK-1-ENYL ETHERS

CROSS-REFERENCE TO RELATED PATENT APPLICATIONS

This application is a continuation-in-part of Ser. No. 417,135, filed on Oct. 4, 1989, abandoned.

In one aspect this invention relates to novel alk-1-enyl ethers which can be cationically cured by heat or light radiation to form coatings and adhesives. In another aspect the invention relates to the reaction composition and the process for preparing said alk-1-enyl ethers.

BACKGROUND OF THE INVENTION

Polyallyl ethers derived from polyols and carbohydrates, particularly allylated pentaerythritol, trimethylpropane, and srarches and sugars have been widely investigated as monomers suitable for protective coatings. These materials are attractive since they undergo autoxidative polymerizarion in contact With air. However, because of slow curing rates, color formation and relatively poor substrare bonding strength, films of these allyl ethers have limited commercial use (see ALLYL COMPOUNDS AND THEIR POLYMERS by C. E. Schildknecht, Wiley Interscience, 1973). Additionally many of these monomers and oligomers are thermally unstable and decompose to give off an objectionable odor characteristic of acrolein.

Attempts to prepare high molecular weight monoallyl ethers by free radical or ionic polymerizations have not been successful and result in low molecular weight products in admixture with substantial quantitites of unreacted material which is difficult to separate. According to British Patent 730,670, the polymerization of a allyl glycidyl ether benzene solution in the presence of 3% ditertiary butyl peroxide at 155° C. resulted in a product having a molecular weight of only 500 which was contaminated with a significant quantity of unconverted allyl glycidyl ether. Obviously such materials are unsuitable as protective coatings.

Although esters, which are electron accepting and require free radical initiation for UV curing, are not comparable to electron donating ethers which are highly reactive in cationically induced reactions, it is noted for the sake of full disclosure that certain ester blends of acrylated bisphenol A epoxy resins and ester blends of acrylated aromatic urethanes have been cured by UV exposure to provide rigid coatings. This work is reported by Byron K. Christmas et. al. in 1988 (Specialty Chemicals 8(1) 24–6). However, these ester blends are not UV curable by cationically induced systems. Thus, as to be expected, their curing rates are comparatively slow, i.e. 7.5–100 ft/min with few exceptions up to 150 ft/min as compared to 300–500 ft/min achieved with cationically initiated UV radiation. Also, the coating properties of these blends display highly unpredictable results ranging from 0%–100% adhesion and MEK resistance from 1 to about 50 in most cases.

Accordingly, it is an object of the present invention to avoid the use of esters and to overcome the above deficiencies by the use of certain alkenyl ethers which can be readily polymerizable in cationically initiated systems to provide thermally stable compounds having superior coating properties.

Another object is to provide films which consistently show good adhesion and high resistance to chemical attack.

Another object of this invention is to provide an economical and commercially feasible process for rapid curing coatings of the present compounds.

Still another object is to provide metal and glass coatings and finishes which are not subject to coloration over extended periods of use.

These and many other objects of the invention will become apparent from the following description and disclosure.

THE INVENTION

In accordance with this invention there is provided a novel, cationically induced radiation curable, alk-1-enyl ether which can be prepared by reacting an alk-1-enyloxy oxirane with a mono- or poly- hydroxylated compound, wherein preferably equimolar amounts of epoxide to the hydroxy group are employed. The reaction is illustrated by the following equation:

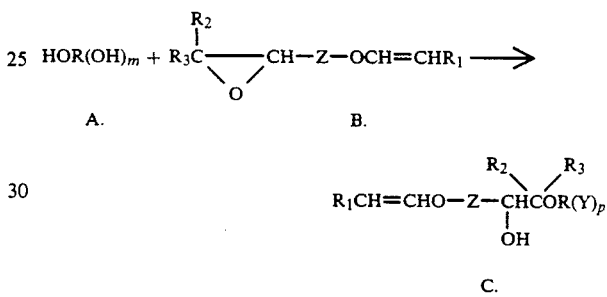

wherein
m and p have a value of from 0 to 8;
when p has a positive value, R is a divalent $C_2$ t $C_{20}$ aromatic or aliphatic hydrocarbon* radical optionally substituted with halo, carbonyl, vinyl ether, carboxylate, hydroxy, alkoxy, alkyleneoxyalkyl and alkenyleneoxyalkyl or the radical

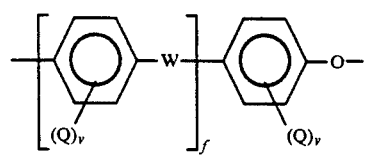

where
W is $C_1$ to $C_4$ alkyl, sulfur, sulfonyl or oxygen;
f has a value of from 1 to 50; Q is halo or $C_1$ to $C_4$ alkyl and v has a value of 0 to 4;
where p is zero, R is a monovalent $C_2$ to $C_{20}$ optionally alkoxylated radical or alkyl, phenyl, benzyl, a polyhydroxylated starch, sugar or cellulose
$R_2$ and $R_3$ are each independently hydrogen, $C_1$ or $C_6$ alkyl, alkenyl, haloalkyl or haloalkenyl;
$R_1$ is hydrogen or $C_1$ to $C_6$ alkyl;
Z is an optionally alkoxylated to $C_1$ to $C_8$ aliphatic hydrocarbon;
Y is hydrogen, hydroxy or

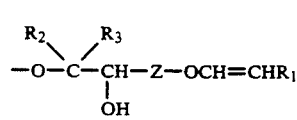

*The term "divalent aliphatic hydrocarbon" as used herein denotes an alkylene, alkylene, alkynylene, aralkylene, aralkenylene radical or the radical —[—C₆H₄—alkylene—]ᵣ—C₆H₄—composed of carbon and hydrogen. The term "divalent aromatic hydrocarbon" denotes an optionally alkyl or alkenyl substituted arylene radical also composed of carbon and hydrogen.

Accordingly, when the condensation reaction employs prop-1-enyloxy methyl oxirane and bisphenol A in a molar ratio of 2:1, the product of the reaction is

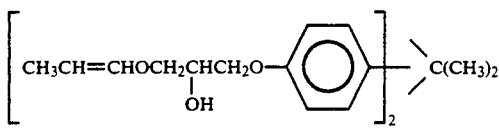

I.

When the condensation reaction is carried out using e.g. 1,1-dihydroxy butane with [4-(ethenyloxy)ethyloxy methyl] oxirane in a mole ratio of 2:1, the reaction product is

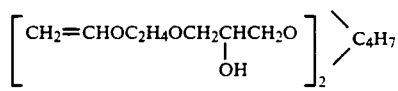

II.

and when the hydrogenated product is for example 1,1,4,6,8-pentahydroxy decane the product will be

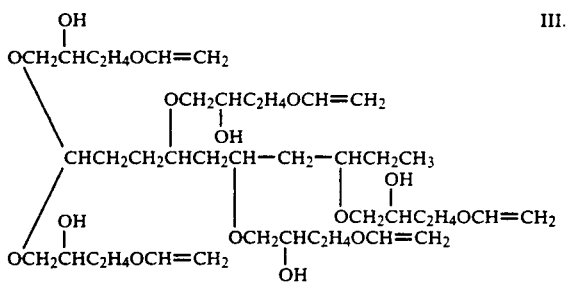

III.

It is to be understood that the products of this invention can be in the form of a cis and trans isomeric mixtures. When other polyols, such as tri and tetra hydroxylated reactants are involved, the same condensation reactions shown above will occur at the hydroxy sites of the hydroxylated reactant.

The following formula VI illustrates a reaction product of a phenol-formaldehyde condensation resin and (prop-1-enyloxy methyl) oxirane, where the molar ratio of oxirane per -OH group is 1:1.

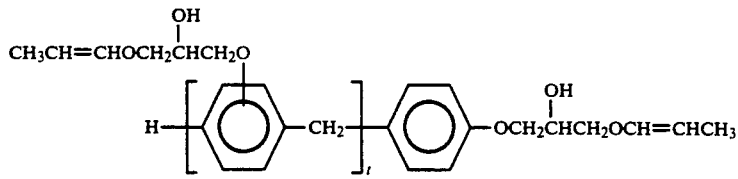

IV.

where t has a value of from 10 to 40.

The product obtained from (prop-1-enyloxy methyl) oxirane and pentaerythritol in molar proportion of 4:1 is

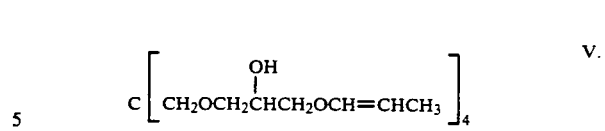

V.

This product may also contain some mono-, di- and/or trisubstituted species, e.g.

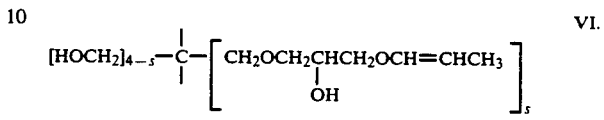

VI.

where s has a value of from 1 to 4.

As pointed out above, the hydroxy reactant can have a linear, branched, cyclic aliphatic or aromatic structure and can be monomeric or polymeric. Examples of suitable hydroxylated reactants include polyalkylene glycols, hydrogenated bisphenol A, halogenated bisphenol A, bisphenol A, alkoxylated bisphenol A, dihydroxyphenyl ether, resorcinol, hydroquinone, tetrahydrofuran dimethanol, petunidin chloride, methyl hydroxypentanol, pentaerythritol, trimethylol propane, trimethylol ethane, dihydroxyethylbenzoate, dihydroxy naphthyl hexanone, phenol, bisphenol, polyphenol, methanol, ethanol, propanol, butanol, octanol, 1,4,6-trihydroxyoctane, 2,2,6,8,10-pentahydroxy dodecane, ethylene glycol, propylene glycol, ethylene chlorohydrin, butanediol, phenaglycodol, butenediol, butynediol, glycerol, glyceryl, hydroxybutyl vinyl ether, monochlorohydrin, cresol, benzyl alcohol, hydroxy-methyl acetophenone, cresyl acetate, cyclohexanol, halogenated phenols, catechol, hexylresorcinol, trihydroxybenzene, a phenol-formaldehyde condensate resin, tetrahydroxybenzene, dihydroxy phenyl methane, trihydroxy butane, tetralol, naphthol, anthranol, etc. and natural alcohols such as cellulose, starches, and sugars and alkoxylated derivatives thereof.

The alk-1-enyloxy oxirane reactant contains from 5 to 28 carbon atoms, examples of which include 1-methyl-2-(prop-1-enyloxy) oxirane, (3-ethenyloxy propyl) oxirane, (4-ethenyloxy-butyloxy) methyl oxirane, 1-butyl-2-[2-(but-1-enyloxy) ethyl] oxirane, [4-(prop-1-enyloxy) butyl] oxirane, [2-(prop-1-enyloxy) ethyl] oxirane, 1-butyl-2[(but-1-enyloxy) ethyl] oxirane, [(prop-1-enyloxy) methyl] oxirane, [2-(vinyloxy) ethyl] oxirane, 1-ethyl-2-[(prop-1-enyloxy)methyl] oxirane, 1-methyl-1-ethyl-2-[3-(hex-1-enyloxy)propyl] oxirane, 1-methyl-2-[2-(but-1-enyloxy) ethyl] oxirane, 1-ethyl-2-[4-(vinyloxy)butyl] oxirane, (ethenyloxy methyl) oxirane, 1-propyl-2-[2-(prop-1-enyloxy) ethyl] oxirane, 1,1-dimethyl-2-[2-(but-1-enyloxy) ethyl] oxirane, 1-hexyl-2-[8-(prop-1-enyloxy) octyl] oxirane, etc.

The mole ratio of hydroxylated compound to oxirane reactant can vary between about 1:1 and about 1:9, depending upon the number of —OH groups in the hydroxylated compound, however, the mole ratio of epoxy per hydroxy is 1:1. In some instances where a polyol is employed, it may be desirable to convert less than all of the hydroxy groups in the compound. In this case less than an oxirane equimolar proportion but an amount sufficient to convert at least one of the hydroxy groups of the polyol is used. Thus a ratio of epoxy/hydroxy can vary between 1:1 and 1:7, a ratio of between 1:1 and 1:3 being more desirable and 1:1 being preferred. Thus, when the hydroxylated compound is a diol, a mole ratio of 1:2 is employed. When the hydroxylated compound is an polyhydroxy alkane containing up to 4 hydroxy groups, e.g. pentaerythritol, tetrahydroxy butane, etc. the mole ratio of hydroxylated alkane to epoxide is 1:4 when it is desired to react all of the hydroxy groups.

The reaction is carried out in the presence of a base catalyst such as, e.g. sodium or potassium metal, sodium or potassium methoxYlate, hYdroxide, alkoxide, hYdride, phenoxide, or an alkaline earth metal hydroxide or alkoxide. Also, alkali or alkaline earth metal salts of reactant A can be employed. The catalyst is employed in a concentration of between about 0.1 and about 5 wt. %, preferably between about 0.4 and about 1 wt. %, based on total reactants.

In cases where the mixture of reactants provides a liquid having a viscosity such that good agitation becomes difficult, up to about 90 wt. % of an inert solvent can be added to the mixture. Suitable solvents include toluene, xylene, benzene; ethers such as alkyl ethers, e.g. methyl ethyl ether, diethyl ether, dibutyl ether, 1,2-dimethoxyethane, bis(2-methoxyethyl) ether, tetrahydrofuran; ketones such as methyl ethyl ketone; amides such as N-methyl-pyrrolidone, dimethyl formamide, N-ethyl-pyrrolidone;esters such as butyrolactone and ethyl acetate; nitriles such as acetonitrile and benzonitrile, cyclic carbonates such as ethylene and propylene carbonates and the like which have a boiling point below that of the reaction product.

The present reaction is effected in the liquid phase by agitating the reactants under a blanket of inert gas, e.g. nitrogen, argon, etc., at a temperature within the range of between about 50° and about 150° C. under from about atmospheric pressure up to about 1,000 psi when volatile reactants are employed in the reaction mixture. The reaction takes place over a period of from about 1 to 48 hours. Preferred reaction conditions include a temperature of between about 90° and about 135° C. under a pressure not exceeding 200 psi for a period of from about 2 to 20 hours.

When the reaction product is highly viscous, any of the above named solvents can be added for dilution and the crude reaction mixture treated to remove catalyst. For example water can be added to the mixture to form a 2-phase liquid and to take up catalyst in the aqueous phase. The organic phase containing product is separated from the aqueous phase and dried to remove water and any solvent which may have been added to lower viscosity is removed under reduced pressure. Alternatively, a weakly acid ion exchange resin, e.g. Amberlite, IRC-50 or an inorganic adsorbent such as Magnesol, can be added to the reaction mixture to pecipitate the catalyst whereupon the desired product is recovered by filtration.

The products of this process are useful as molding resins, adhesives and as highly solvent resistant coating materials which undergo substantially instantaneous curing thermally or curing by irradiation in cationically initiated systems to provide clear, colorless, flexible films when applied to a substrate.

Having thus generally described the invention, reference is now had to the accompanying examples which illustrate preferred embodiments but which are not to be construed as limiting to the scope of the invention as more broadly set forth above and in the accompanying examples.

EXAMPLE I

In a 500 ml 3-necked round bottomed glass flask equiped with a mechanical stirrer, a thermometer, a water condenser and a nitrogen inlet is mixed 57 g. of bisphenol A, 62 g. of 74%-26% cis/trans [(prop-1-enyloxy)methyl] oxirane (mole ratio of 1:2). To this mixture, 2.5 g. of NaOCH$_3$ is added and the resulting mixture agitated under a blanket of nitrogen. After 12 hours at 130° C. under ambient pressure proton NMR indicates completion of the reaction and 250 cc of toluene is then added. The reaction product is recovered by washing with three 250 g. portions of H$_2$O, thus forming an aqueous phase and an organic phase. The organic layer containing product is separated, dried with magnesium sulfate, filtered and toluene is evaporated under reduced pressure. A clear liquid product having the formula

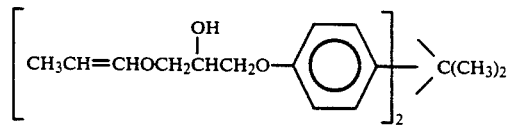

is recovered.

The above reaction is repeated except that 54%-46% cis/trans [(prop-1-enyloxy)methyl] oxirane is substituted. The substitution of this reactant has no material affect and the product is identical to that described above except for the cis/trans product distribution.

EXAMPLE II

Example I is repeated except that 57 g. of the oxirane reactant is employed to provide a 1:2 mole ratio and resorcinol is substituted for bisphenol A. The product having the formula

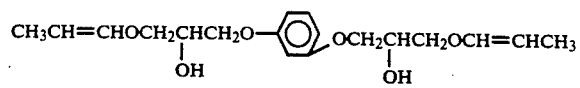

is recovered in 95% yield.

EXAMPLE III

A 500 ml 3-necked round bottomed flask equipped with a mechanical stirrer, thermometer, water condenser and nitrogen inlet is charged with 114 g. (0.5 mole) of bisphenol A, 100 g. (1.05 moles) of [(eth-1-enyloxy)methyl] oxirane (74%-26% cis/trans), i.e. a mole ratio of 1:2, and 2.5 g. of sodium methoxide. The flask is heated to 130° C. and stirred for 5 hours under nitrogen. Progress of the reaction is monitored by withdrawing samples of the reaction mixture every hour via proton NMR. The product mixture is then diluted with 250 ml of toluene.

The product is recovered by washing with three 250 g. portions of water. The resulting organic layer is separated from the aqueous layer and dried with magnesium sulfate, filtered, and the toluene removed under reduced pressure. The final product (200 g.) is a clear yellow viscous liquid having the formula

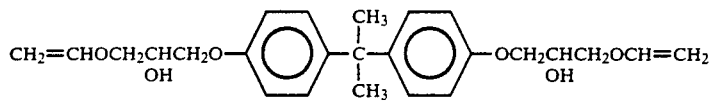

Other examples employing different cis/trans ratios, e.g. 54%–46%, can be employed without affect on the product obtained.

EXAMPLE IV

To a glass reactor equipped with a thermometer, mechanical stirrer, condenser and nitrogen inlet 114 g. of [(prop-1-enyloxy)methyl] oxirane, 34 g. of pentaerythritol, and 0.5 g. sodium methoxide are charged. This mixture is stirred and heated to 115° C. under nitrogen for 5 hours. The catalyst is removed by slurrying with Magnesol and tetrahydrofuran followed by filtration and solvent evaporation after which a clear yellow liquid product having the formula

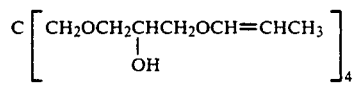

is obtained.

EXAMPLE V

In a 1 liter glass reactor equipped with a mechanical stirrer, thermometer, condenser, and nitrogen inlet is added 127 g. of phenol, 342 g. of [(prop-1-enyloxy)methyl] oxirane and 25 g. of sodium methoxide. This mixture is stirred at room temperature under a blanket of nitrogen for 7 hours. Exothermic conditions cause the temperature of the reaction mixture rise to 150° C. After 3 hours the reaction is cooled to about room temperature whereupon the product is recovered in 90% yield by flash distillation under reduced pressure. Proton NMR spectroscopy shows the product to have the structure:

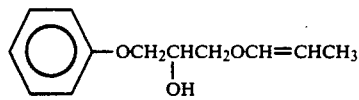

EXAMPLE VI

In a 500 cc glass reactor equipped with a mechanical stirrer, condenser, nitrogen inlet, and thermometer is added 114 g. of bisphenol A, 57 g. of (prop-1-enyloxy)methyl] oxirane and 200 g. cc of 2-methoxyethyl ether. This mixture is stirred at 120° C. for 6 hours under nitrogen gas. The product having the formula

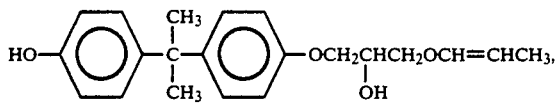

including a minor amount of the disubstituted product, is recovered using the procedure of Example IV.

It will be understood that many modifications and substitutions can be made in the above examples to provide the novel compounds of this invention. For example, other oxiranes, such as [(but-1-enyloxy)butyl] oxirane, [(pent-1-enyloxy)butenyl] oxirane, [(prop-1-enyloxy)methyl] dimethyl oxirane, butenyloxy ethyl epoxide and the like can be substituted in any of the foregoing examples. Also, other hydroxylated compounds can be substituted therein. For example monohydroxylated and polyhydroxylated alkanes of 2 or more carbon atoms, a starch or a sugar, an polyethoxylated or polypropoxylated butanediol, dichlorobutanediol, and the like are representative. All of the above are included in the scope of this invention.

What is claimed is:

1. The alk-1-enyl ether having the formula

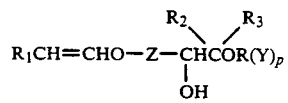

wherein p has a value of from 0 to 8:

when p has a positive value, R is a divalent $C_2$ to $C_{20}$ aromatic or aliphatic hydrocarbon radical optionally substituted with halo, carbonyl, vinyl ether, carboxylate, hydroxy, alkoxy, alkyleneoxyalkyl and alkenyleneoxyalkyl or the radical

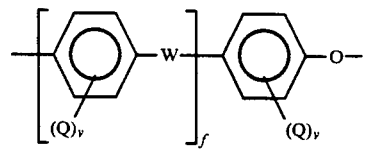

where

W is $C_1$ to $C_4$ alkyl, sulfur, sulfonyl or oxygen;

f has a value of from 1 to 50; Q is halo or $C_1$ to $C_4$ alkyl and v has a value of 0 to 4;

when p is zero, R is a monovalent $C_2$ to $C_{20}$ alkoxylated radical or alkyl, phenyl, benzyl, a polyhydroxylated starch, sugar or cellulose radical

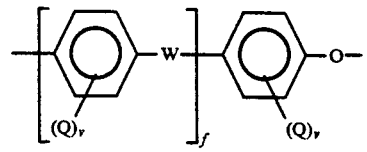

where

W is $C_1$ to $C_4$ alkyl, sulfur, sulfonyl or oxyen;

f has a value of from 1 to 50; Q is halo or $C_1$ to $C_4$ alkyl and v has a value of 0 to 4;

$R_2$ and $R_3$ are each independently, $C_1$ to $C_6$ alkyl, alkenyl, haloalkyl or haloalkenyl;

$R_1$ is hydrogen or $C_1$ or $C_6$ alkyl;

Z is an optionally alkoxylated $C_1$ to $C_8$ aliphatic hydrocarbon;

Y is hydroxy or

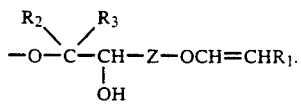

2. The alk-1-enyl ether of claim 1 wherein p has a positive value.

3. The alk-1-enyl ether of claim 2 wherein R is

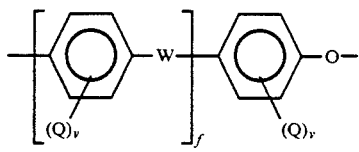

4. The alk-1-enyl ether of claim 3 wherein R is the divalent radical of bisphenol A.

5. The alk-1-enyl ether of claim 4 having the formula

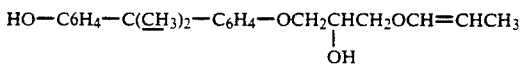

6. The alk-1-enyl ether of claim 4 having the formula

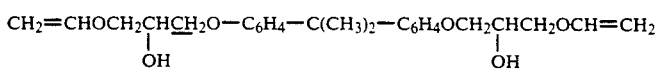

7. The alk-1-enyl ether of claim 2 wherein R is the divalent radical of resorcinol.

8. The alk-1-enyl ether of claim 2 whwerein p has a value of from 1 to 3, R is an aliphatic hydrocarbon and Y is

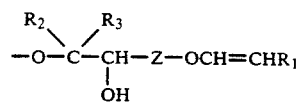

9. The alk-1-enyl ether of claim 2 wherein p has a value of 3, R is —$CH_2C(CH_2)_3$— and Y is a mixture of hydroxy and

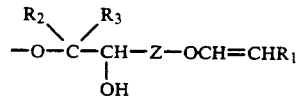

radicals.

10. The alk-1-enyl ether of claim 2 having the formula

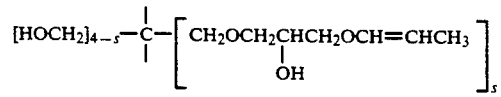

where s has a value of 1 to 4.

11. The alk-1-enyl ether of claij 10 which has the formula

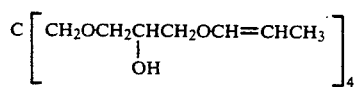

12. The alk-1-enyl ether of claim 1 wherein p is zero and R is phenyl.

13. The alk-1-enyl ether of claim 12 having the formula

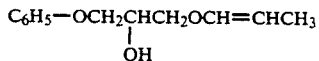

* * * * *